Aug. 21, 1973 A. H. SYLVESTER Plant Pat. 3,388
PEACH TREE
Filed Feb. 8, 1972
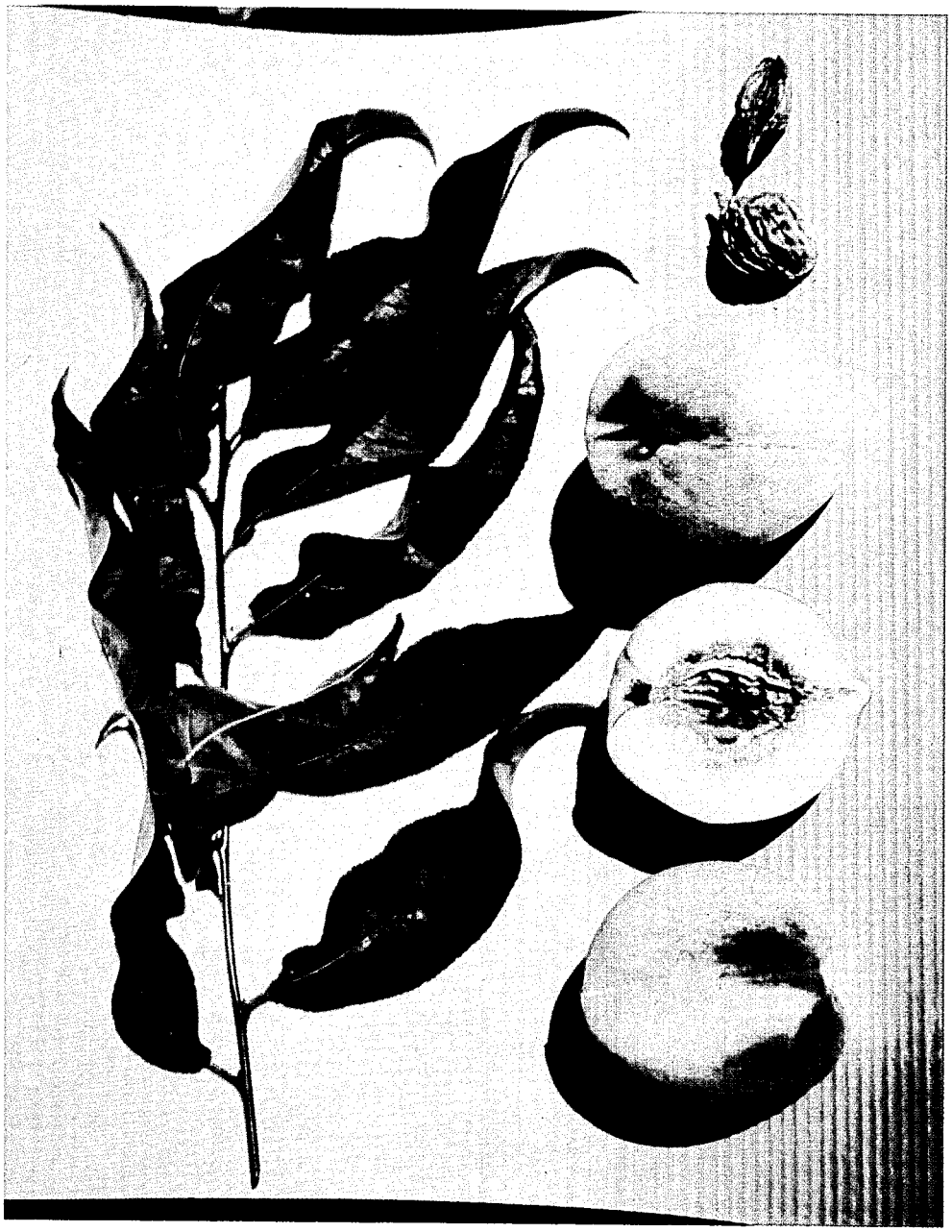

United States Patent Office

Plant Pat. 3,388
Patented Aug. 21, 1973

3,388
PEACH TREE

Arley H. Sylvester, deceased, late of Hotchkiss, Colo., by Roderick N. Stewart, Delta, Colo., executor, assignor to Stark Bros. Nurseries & Orchards Co., Louisiana, Mo.

Filed Feb. 8, 1972, Ser. No. 224,631
Int. Cl. A01h 5/03
U.S. Cl. Plt.—43 1 Claim The present invention relates to a new and distinct variety of peach tree of the yellow-fleshed, freestone, fruit-bearing type, which was originated by the late Arley H. Sylvester, deceased, from seed of the peach variety known as "Elberta" (unpatented) planted by her on her cultivated property located at Hotchkiss, Delta County, Colo.

As the result of this seed planting aforementioned, there was produced a new and improved peach variety which generally resembles its parent variety "Elberta," but which is distinguished therefrom, as well as from all other peach varieties heretofore in commerce, as evidenced by the following unique combination of characteristics, among others, which are outstanding in the new variety:

(1) A later fruit ripening habit usually ranging from about 10 to 14 days later than "Elberta";

(2) Firm, clear yellow fruit flesh, with only a trace of pink color on the surface of the pit cavity, and complete absence of red color in the flesh as compared to the heavily stained red flesh near the pits of the fruit of "Elberta";

(3) An excellent fruit flavor, with less bitterness than the flavor of "Elberta" fruit; and (4) Good shipping qualities of the fruit.

Asexual reproduction of the new variety, as performed by budding at Hotchkiss, Colo., shows that the foregoing characteristics and distinctions come true to form and are established and transmitted through succeeding propagations.

The accompanying drawing shows typical specimens of the foliage, fruit and pits of the new variety as depicted in color, with the fruit specimens being shown in elevation, as well as in cross section.

The following is a detailed description of the new variety, with color terminology in accordance with Ridgway's Color Standards and Nomenclature (hereinafter abbreviated as (R)), and Horticultural Colour Guide (hereinafter abbreviated as (HCG)), except where general color terms of ordinary dictionary significance are obvious, and based on observations made from specimens grown at Hotchkiss, Colo.:

Dates of first and last pickings: September 22 and September 28, respectively.

Tree: Medium large; vigorous; dense; open; spreading; vase-formed; hardy; productive; regular bearer.

*Trunk.*—Medium stockiness; medium smoothness.

*Branches.*—Medium stockiness; smooth. Color—Tawny-Olive, Plate XXXIX, No. 17", tone i (R).

*Lenticels.*—Medium number; medium large.

*Leaves.*—Medium large; ovate; acutely pointed; medium thickness. Length—from 5½ inches to 6½ inches. Width—1¼ inches. Color—Parsley Green, Green, Plate 00962/1, page 193, vol. II (HCG). Margin—finely serrate. Petiole—medium short; medium thickness. Glands—average 2 in number; alternate; medium large; reinform; appressed.

Flowers: Medium early; large.

*Dates of first and full bloom.*—May 5 and May 10, respectively.

*Color.*—Pink.

Fruit:

*Maturity when described.*—Eating ripe.

*Size.*—Variable; medium large.

Axial diameter—from 3 inches to 3⅜ inches. Transverse diameter in suture plane—from 2⅝ inches to 2¾ inches. Diameter at right angles to suture plane—from 2½ inches to 3 inches.

*Form.*—Unsymmetrical; broadly ovoid.

*Suture.*—Distinct; extends from base to beyond apex.

*Ventral surface.*—Rounded; slightly lipped toward apex; lips unequal.

*Cavity.*—Abrupt; elongated in suture plane; with suture showing on both sides. Depth—9/16 inch. Breadth—1 inch. Markings—none.

*Base.*—Cuneate; truncate; oblique.

*Apex.*—Prolonged; apical.

*Stem.*—Stout; about ⅜ inch long; pubescent; medium strong adherence to stone.

*Skin.*—Medium thin; medium tender; no tendency to break. Color—Claret Rose, Plate 021, page 109, vol. II (HCG). Down—abundant; medium short; does not roll up when rubbed.

*Flesh.*—Color—Straw yellow, Plate 604/1, page 67, vol. I (HCG). Surface of pit cavity—color—Yellow, with pink fibers. Amygadlin—wanting. Juice—moderate abundance. Texture—meaty. Fibers—few; fine; tender. Ripens—evenly. Flavor—subacid. Aroma—distinct. Eating quality—good.

*Stone.*—Free. Fibers—long; free. Size—medium large. Length—1¾ inches. Thickness—⅞ inch. Form—oval; cuneate toward base. Base—oblique. Hilum—oval. Apex—acute. Sides—some equal and some unequal. Surface—irregularly furrowed near base; pitted throughout. Ridges—rounded. Pits—elongated. Ventral edge—thick; with wing throughout. Dorsal edge—full; with narrow groove throughout. Ridges on either side—interrupted.

Use: Market; dessert; canning.

Keeping quality: Good.

Shipping quality: Good.

What is claimed is:

1. A new and distinct variety of peach tree of the yellow-fleshed, freestone, fruit-bearing type, substantially as herein shown and described, characterized particularly as to novelty by its general resemblance to its parent variety "Elberta," but being principally distinguished therefrom by the unique combination of a later fruit ripening habit usually ranging from about 10 to 14 days later than "Elberta," firm, clear yellow fruit flesh, with only a trace of pink color on the surface of the pit cavity, and complete absence of red color in the flesh as compared to the heavily stained red flesh near the pits of the fruit of "Elberta," an excellent fruit flavor, with less bitterness than the flavor of "Elberta" fruit, and good shipping qualities of the fruit.

No references cited.

ROBERT E. BAGWILL, Primary Examiner